(12) United States Patent
Morelli et al.

(10) Patent No.: US 8,812,111 B2
(45) Date of Patent: Aug. 19, 2014

(54) IMPLANTABLE CARDIOVERTER DEFIBRILLATOR CAPACITOR ASSEMBLY WITH FLEX CIRCUIT

(71) Applicant: Medtronic, Inc., Minneapolis, MN (US)

(72) Inventors: Douglas James Morelli, Forest Lake, MN (US); William Richard Schildgen, Chisago City, MN (US); Stephen D Hall, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/020,022

(22) Filed: Sep. 6, 2013

(65) Prior Publication Data

US 2014/0043726 A1    Feb. 13, 2014

Related U.S. Application Data

(63) Continuation of application No. 12/607,336, filed on Oct. 28, 2009, now Pat. No. 8,532,777.

(30) Foreign Application Priority Data

Oct. 29, 2009    (WO) ................ PCT/US2009/062538

(51) Int. Cl.
*A61N 1/365* (2006.01)
*A61N 1/375* (2006.01)
(52) U.S. Cl.
CPC .............. *A61N 1/375* (2013.01); *A61N 1/3758* (2013.01)
USPC ........................................... 607/36

(58) Field of Classification Search
USPC .............. 607/2, 5, 36, 37, 115; 361/500, 503, 361/508, 509
See application file for complete search history.

(56) References Cited

U.S. PATENT DOCUMENTS

| 6,746,797 B2 | 6/2004 | Benson et al. |
| 2003/0040779 A1 | 2/2003 | Engmark et al. |
| 2004/0068302 A1 | 4/2004 | Rodgers et al. |

FOREIGN PATENT DOCUMENTS

EP    1 053 763 A2    11/2000

OTHER PUBLICATIONS (PCT/US2009/062538) PCT Notification of Transmittal of the International Search Report and the Written Opinion of the International Searching Authority.

*Primary Examiner* — Christopher D Koharski
*Assistant Examiner* — Jeremiah Kimball
(74) *Attorney, Agent, or Firm* — Carol F. Barry

(57) ABSTRACT

An implantable cardioverter defibrillator ("ICD") comprises a battery, control circuitry and a capacitor assembly. The capacitor assembly includes at least one capacitor, a flex circuit for connection to the control circuitry of the ICD and a first and second support portions. The flex circuit is arranged between the first and second support portions and includes a plurality of tangs for connecting to the anode and cathode of the capacitor(s), as well as to the control circuitry of the ICD.

20 Claims, 7 Drawing Sheets

US 8,812,111 B2

IMPLANTABLE CARDIOVERTER DEFIBRILLATOR CAPACITOR ASSEMBLY WITH FLEX CIRCUIT

RELATED APPLICATION

This application is a continuation of U.S. patent application Ser. No. 12/607,336, filed Oct. 28, 2009 entitled "IMPLANTABLE CARDIOVERTER DEFIBRILLATOR CAPACITOR ASSEMBLY WITH FLEX CIRCUIT", herein incorporated by reference in its entirety.

FIELD

The present disclosure relates to implantable cardioverter defibrillators ("ICD") and, more particularly, to an ICD that includes a capacitor assembly that is easily and inexpensively manufactured.

INTRODUCTION

This section provides information related to the present disclosure which is not necessarily prior art.

An implantable cardioverter defibrillator ("ICD") provides therapies for maintaining and restoring normal cardiac rhythms by passing or by delivering electrical shock therapy for cardioverting or defibrillating the heart. A typical ICD is implanted in the body and one or more electrical leads connected to the ICD are inserted into or in proximity to the heart of the patient. The leads carry current from the ICD to the heart tissue to stimulate the heart using either low energy pacing pulses or high energy cardioversion/defibrillation shocks. The leads are also used for sensing electrocardiogram signals from the heart that are used by the ICD to determine therapy to be delivered.

It would be desirable to produce an inexpensive and easily manufacturable ICD in which connections can be made reliable.

SUMMARY

This section provides a general summary of the disclosure, and is not a comprehensive disclosure of its full scope or all of its features.

In various embodiments of the present disclosure, a capacitor assembly for use in an implantable cardioverter defibrillator ("ICD") is disclosed. The capacitor assembly comprises at least one capacitor, a flex circuit and first and second support portions. The at least one capacitor comprises a base portion mated with a cover portion at a weld joint to form a housing, a cathode, an anode, and a pin extending from the housing. The housing is electrically connected to the cathode and the pin is electrically connected to the anode of the capacitor. The flex circuit comprises a first tang that is electrically connected to the anode, a second tang that is electrically connected to the cathode, and at least two terminal tangs for connection to control circuitry of the ICD. The first support portion is arranged between the at least one capacitor and a first side of the flex circuit such that the at least one capacitor and the flex circuit are spaced a predetermined distance apart. Further, the first support portion defines an opening through which the second tang extends to electrically connect to the cathode. The second support portion is arranged on a second side of the flex circuit and comprises a first support side that supports the at least two terminal tangs.

In various further embodiments of the present invention, an implantable cardioverter defibrillator ("ICD") is disclosed. The ICD comprises a battery, a control circuit for controlling operation of the ICD that is operably connected to the battery, and a capacitor assembly operably connected to the battery and control circuit. The capacitor assembly comprises at least one capacitor, a flex circuit and first and second support portions. The at least one capacitor comprises a base portion mated with a cover portion at a weld joint to form a housing, a cathode, an anode, and a pin extending from the housing. The housing is electrically connected to the cathode and the pin is electrically connected to the anode of the capacitor. The flex circuit comprises a first tang that is electrically connected to the anode, a second tang that is electrically connected to the cathode, and at least two terminal tangs for connection to control circuitry of the ICD. The first support portion is arranged between the at least one capacitor and a first side of the flex circuit such that the at least one capacitor and the flex circuit are spaced a predetermined distance apart. Further, the first support portion defines an opening through which the second tang extends to electrically connect to the cathode. The second support portion is arranged on a second side of the flex circuit and comprises a first support side that supports the at least two terminal tangs.

In various other embodiments of the present disclosure, an electrochemical cell assembly for use in an implantable cardioverter defibrillator ("ICD") is disclosed. The electrochemical cell assembly comprises at least one electrochemical cell, a flex circuit and first and second support portions. The at least one electrochemical cell comprises a base portion mated with a cover portion at a weld joint to form a housing, a cathode, an anode, and a pin extending from the housing. The housing is electrically connected to the cathode and the pin is electrically connected to the anode of the capacitor. The flex circuit comprises a first tang that is electrically connected to the anode, a second tang that is electrically connected to the cathode, and at least two terminal tangs for connection to control circuitry of the ICD. The first support portion is arranged between the at least one electrochemical cell and a first side of the flex circuit such that the at least one electrochemical cell and the flex circuit are spaced a predetermined distance apart. Further, the first support portion defines an opening through which the second tang extends to electrically connect to the cathode. The second support portion is arranged on a second side of the flex circuit and comprises a first support side that supports the at least two terminal tangs.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
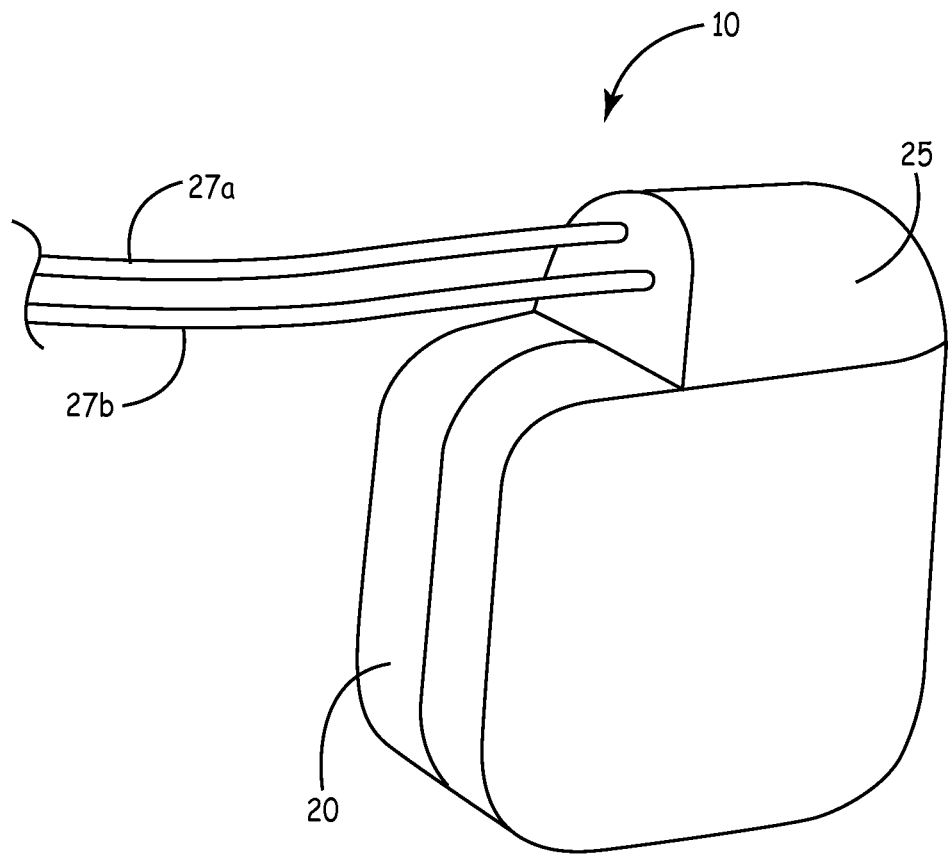
FIG. 1 is a diagram of an ICD and lead set in which the capacitor assembly according to some embodiments of the present disclosure can be included.

Example embodiments will now be described more fully with reference to the accompanying drawings.

Example embodiments are provided so that this disclosure will be thorough, and will fully convey the scope to those who are skilled in the art. Numerous specific details are set forth, such as examples of specific components, devices, and methods, to provide a thorough understanding of embodiments of the present disclosure. It will be apparent to those skilled in the art that specific details need not be employed, that example embodiments can be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a", "an" and "the" can be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps can be employed.

When an element or layer is referred to as being "on", "engaged to", "connected to" or "coupled to" another element or layer, it can be directly on, engaged, connected or coupled to the other element or layer, or intervening elements or layers can be present. In contrast, when an element is referred to as being "directly on," "directly engaged to", "directly connected to" or "directly coupled to" another element or layer, there can be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, can be used herein for ease of description to describe one element or feature's relationship to another element(s) or feature(s) as illustrated in the figures. Spatially relative terms can be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Referring now to FIG. 1, an ICD 10 is illustrated. The ICD 10 includes a housing 20, header portion 25, and electrodes 27a and 27b connected to header portion 25. The header portion 25 operates as a feedthrough to connect the electrodes 27a, 27b to the power and control circuitry present in housing 20. Typically the housing contains at least one battery, sensing and control circuitry and a capacitor assembly. These components are connected to electrodes 27a, 27b in header portion 25. Because of the intricate and sensitive circuitry in the ICD 10, and the fact that all electrical connections must be hermetically sealed, connections between electrodes 27a, 27b and the control and power circuitry within the housing 20 are typically difficult and expensive to manufacture. For example, the minute size of the leads between the control circuitry and electrodes 27a, 27b can require a laser welding process. A laser welding process, while expensive, is typically used due to the fact that other welding or connection processes can result in unreliable connections and/or heat related damage to sensitive electronics. In addition, space limitations of the design space may not allow for other connection processes that require mechanical methods such as electrodes used in Resistance Spot Welding ("RSW").

Figure 2:
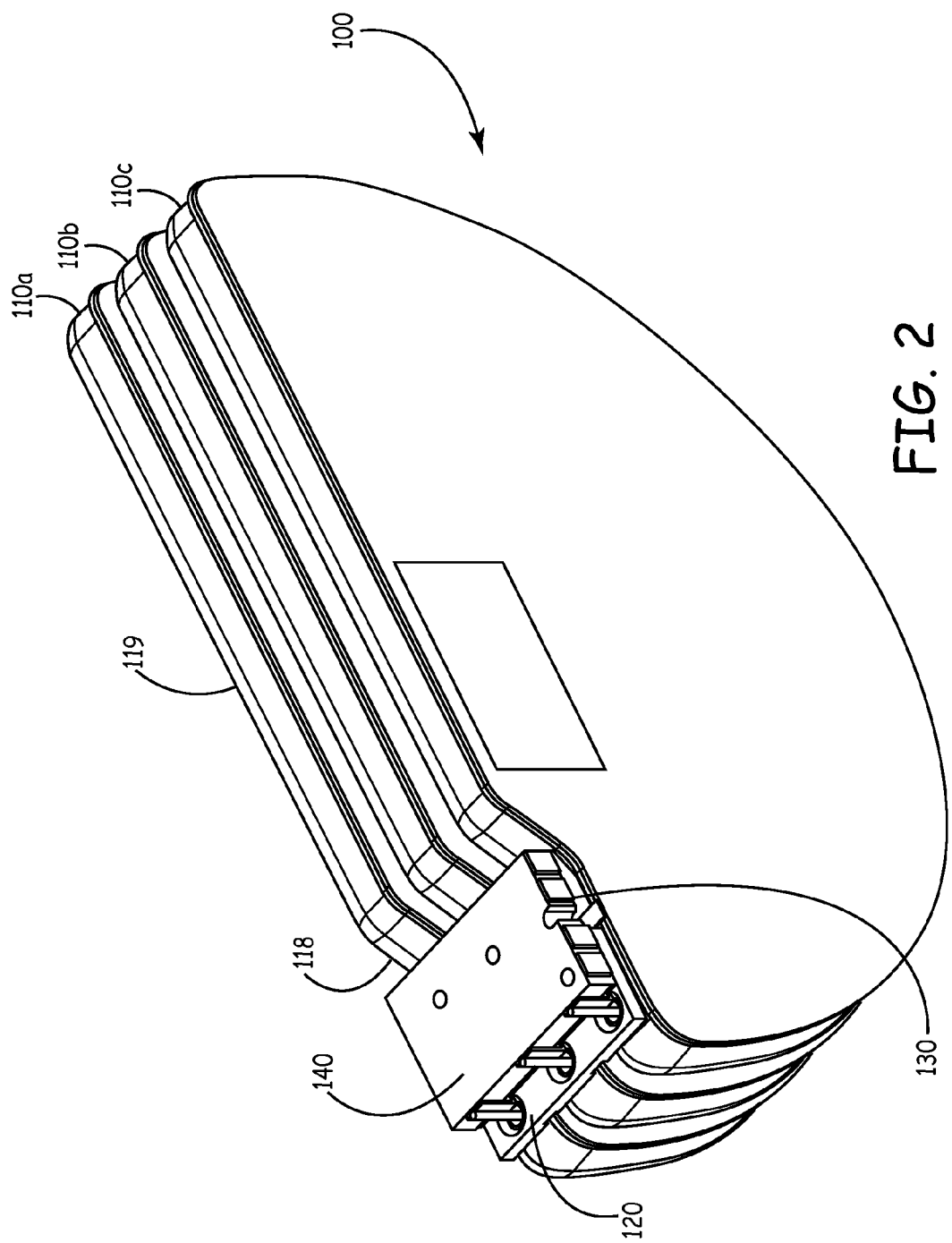
FIG. 2 is a perspective view of a capacitor assembly according to some embodiments of the present disclosure.

Referring now to FIG. 2, a capacitor assembly 100 for use in an implantable cardioverter defibrillator ("ICD"), such as that illustrated in FIG. 1, according to various embodiments of the present disclosure is illustrated. Capacitor assembly 100 comprises three capacitors 110a, 110b, 110c, a first support portion 120, a flex circuit 130 and a second support portion 140. Capacitors 110a-110c are used to store charge from a power source, such as a battery (not shown), that can be used to shock the heart of a patient in which the ICD is implanted. In some embodiments, an electrochemical cell assembly (not shown) can be substituted for capacitor assembly 100. In an exemplary electrochemical cell assembly, an electrochemical cell or battery will function similarly to the capacitor(s) present in the capacitor assembly, e.g., storage and delivery of an electrical charge. While the remainder of this description discusses capacitor assembly 100, it should be appreciated that the replacement of the capacitor assembly 100 with an electrochemical cell assembly is included within the scope of this disclosure.

Figure 3:
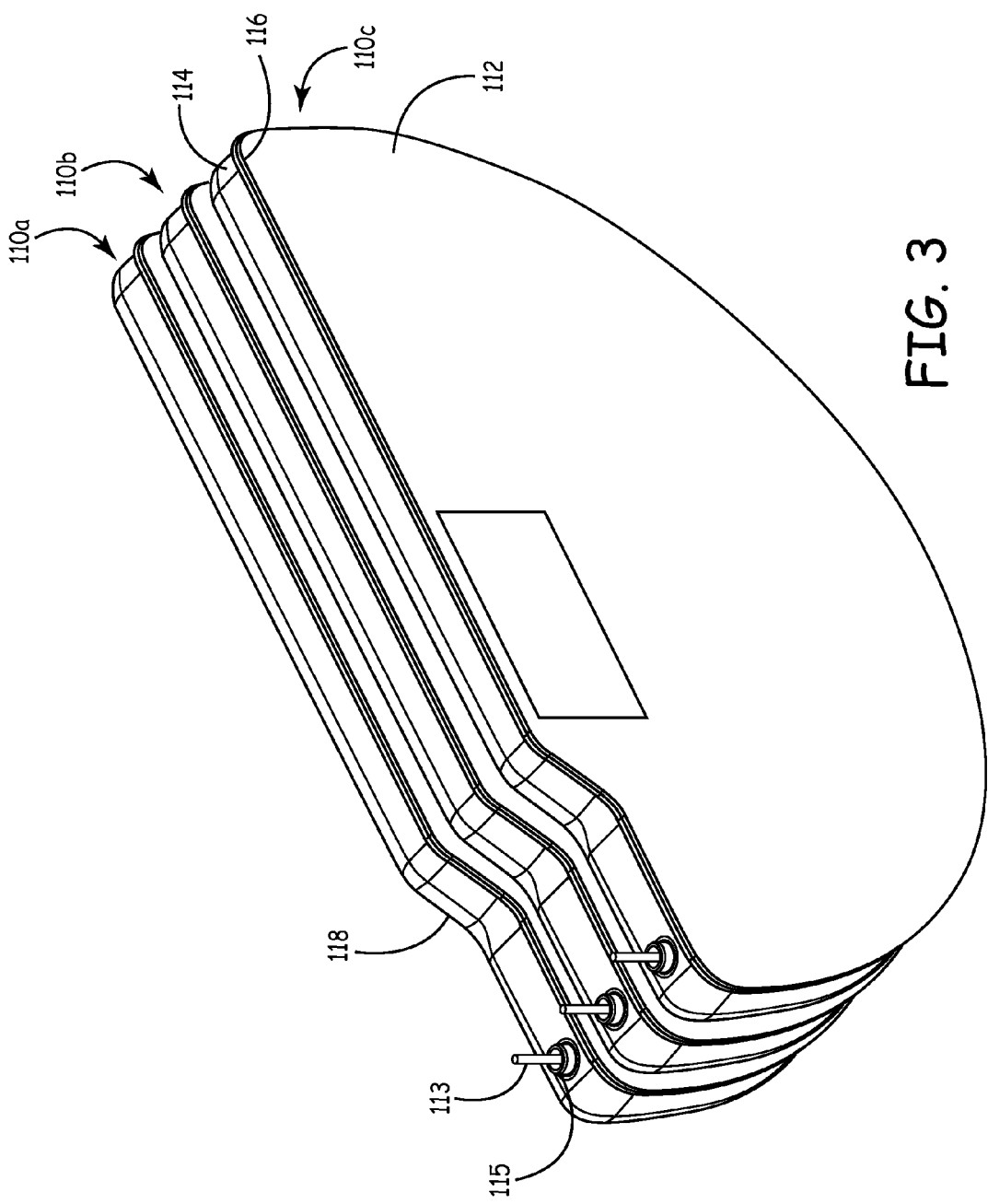
FIG. 3 is a perspective view of a plurality of capacitors forming part of a capacitor assembly according to some embodiments of the present disclosure.

Referring now to FIG. 3, capacitors 110a-110c are illustrated. Each of capacitors 110a-110c are formed by mating a base portion 114 with a cover portion 112 to form a housing. Within the housing, the electrical components, e.g., anode and cathode plates, of the capacitor are present. The base portion 114 and cover portion 112 can be mated by a welding process to form a weld joint 116. In some embodiments, the housing is electrically connected to the cathode of capacitors 110a-110c. A pin 113 can extend through the housing and be electrically connected to the anode of each of the capacitors 110a-110c. In some embodiments, a ferrule 115 surrounds the pin 113 to separate and electrically insulate the pin 113 from the housing. A sloped portion 118 of the housing of capacitors 110a-110c defines a cutout that can receive the flex circuit 130 and support portions 120, 140 such that the capacitor assembly 100 maintains a small profile.

Figure 4:
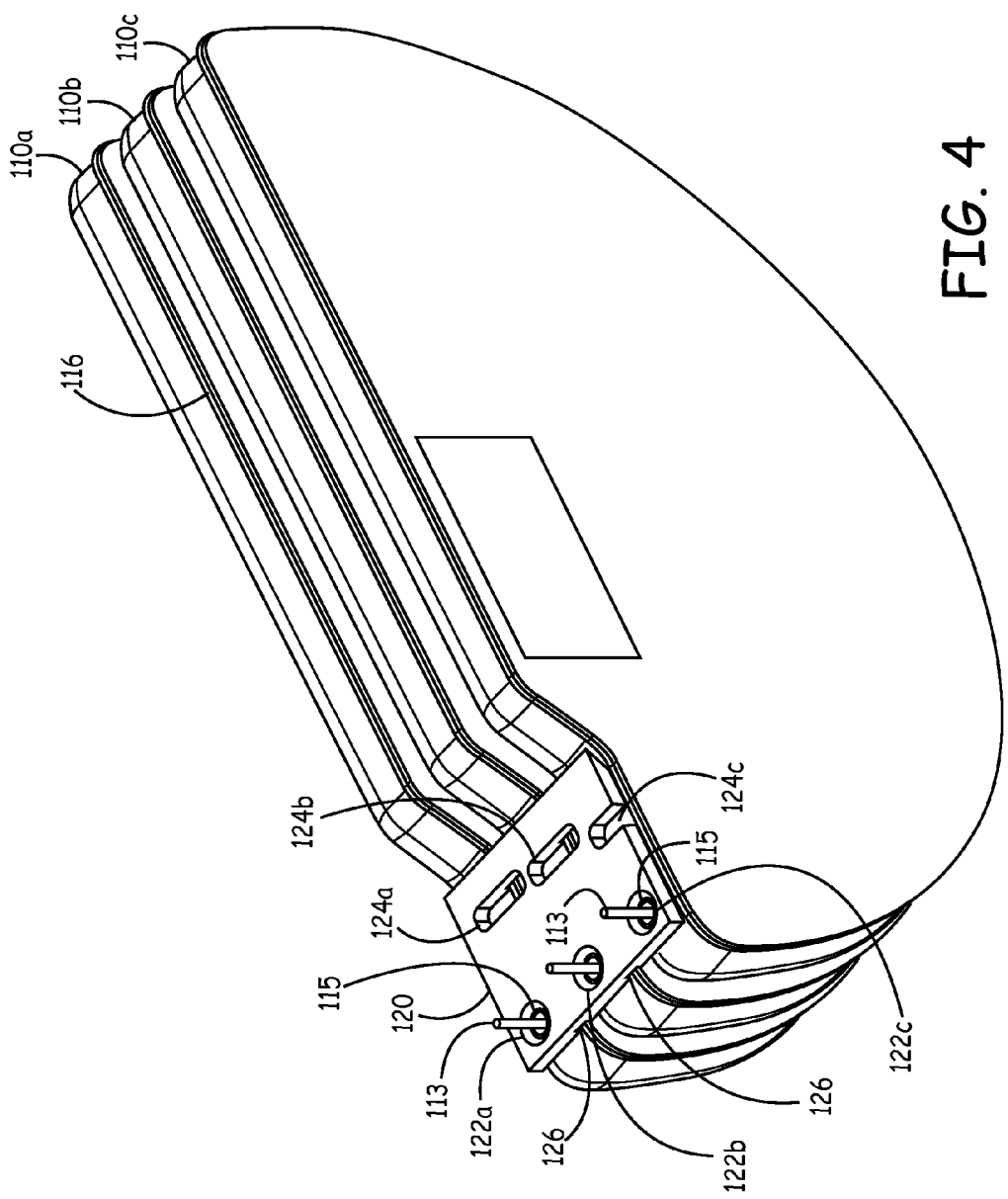
FIG. 4 is a perspective view of a plurality of capacitors and a first support portion forming part of a capacitor assembly according to some embodiments of the present disclosure.

Referring now to FIG. 4, the subassembly of capacitor 110a-110c with an attached first support portion 120 is illustrated. The first support portion 120 is arranged such that the pins 113 are received through openings 122a-122c. Openings 122a-122c are designed to cooperate with ferrules 115 such that the first support portion 120 is precisely aligned with capacitors 110a-110c. First support portion 120 can further include additional cathode openings 124a-124c that allow access to the housing of the capacitors 110a-110c. In some embodiments, the first support portion 120 can include one or more recesses 126 that further cooperate with capacitors 110a-110c. In the illustrated embodiment, recesses 126 are complementary to weld joints 116, which can comprise a flange extending from the housing of the capacitors 110a-110c.

Figure 5:
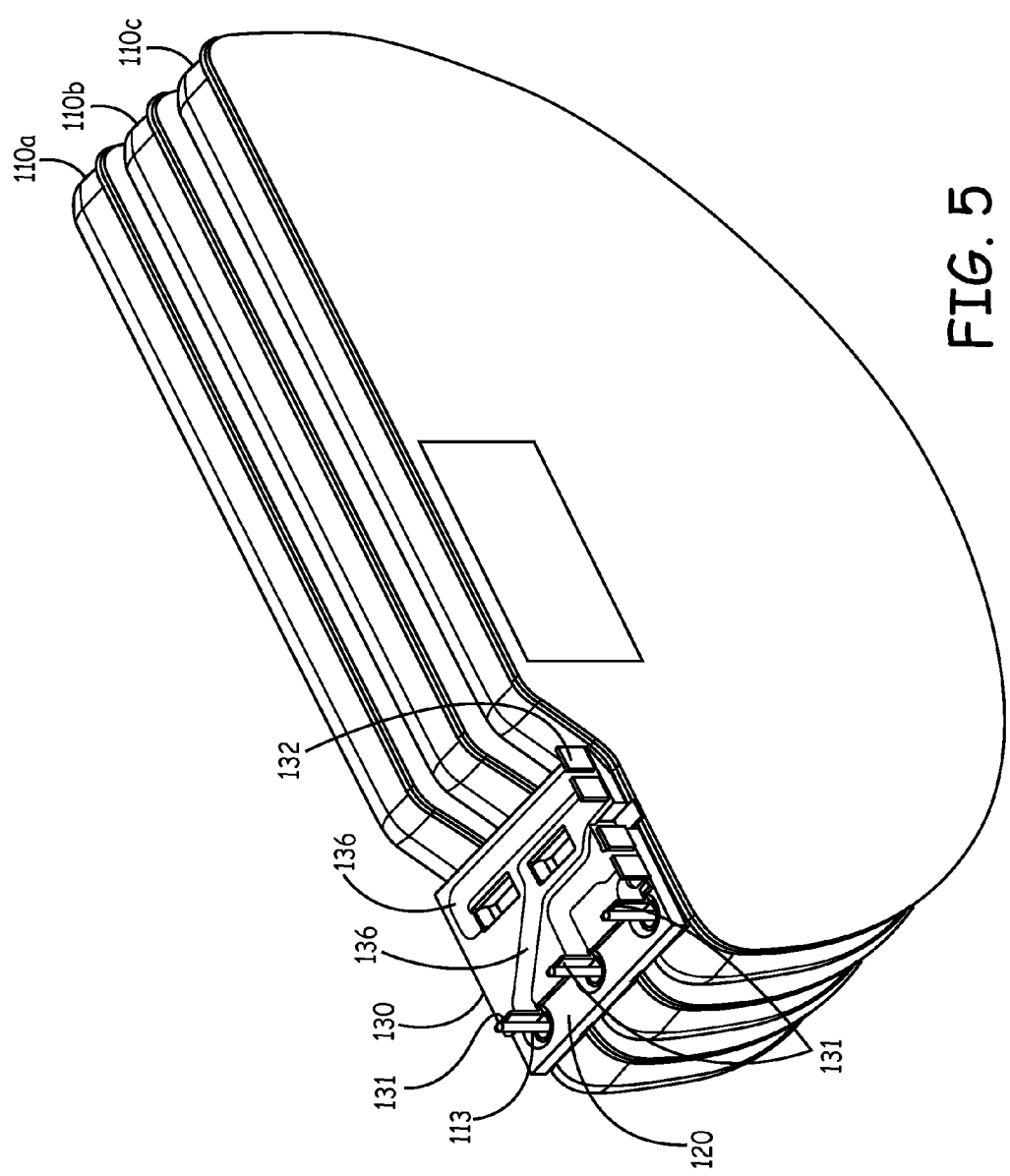
FIG. 5 is a perspective view of a plurality of capacitors, a first support portion, and a flex circuit forming part of a capacitor assembly according to some embodiments of the present disclosure.
Figure 6:
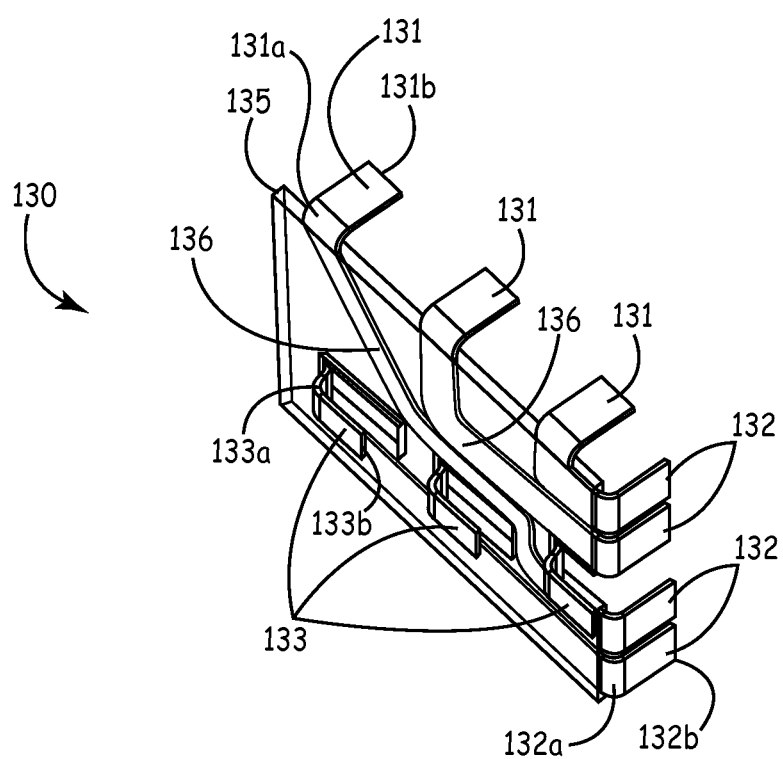
FIG. 6 is a perspective view of a flex circuit that can be included in a capacitor assembly according to some embodiments of the present disclosure.
Figure 7:
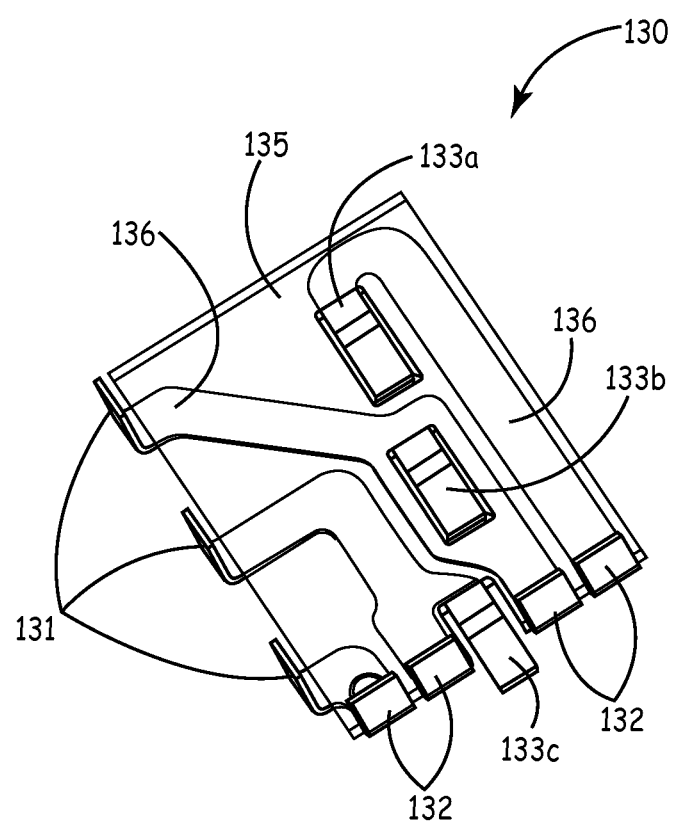
FIG. 7 is another perspective view of a flex circuit that can be included in a capacitor assembly according to some embodiments of the present disclosure.

Referring now to FIGS. 5-7, an exemplary embodiment of flex circuit 130 attached to first support portion 120 and capacitors 110a-110c is illustrated. Flex circuit 130 can include one or more tangs 131 for connecting to the anode pins 113 of capacitors 110a-110c. These tangs 131 can extend from the main body 135 FIGS. 6-7) of flex circuit 130 and be free floating extensions of the traces 136. A tang 131 that is a free floating extension of the traces 136 can have a first end 131a that is attached to the flex circuit 130 and a second end 131b that is unattached. In the illustrated embodiment, tangs 131 extend from the body 135 of flex circuit 130 and are bent substantially perpendicular to the plane of the flex circuit 130. Flex circuit 130 also includes one or more terminal tangs 132 that can be formed similarly to anode tangs 131. In the illustrated embodiment, terminal tangs 132 are connected to anode tangs 131 by traces 136 and are formed as free floating extensions that are capable of movement independent of the main portion of flex circuit 130. A tang 132 that is a free floating extension can have a first end 132a that is attached to the flex circuit 130 and a second end 132b that is unattached. Terminal tangs 132 provide the interconnection between capacitors 110a-110c and the power and control circuitry of the ICD (not shown).

Flex circuit 130 can also include at least one cathode tang 133 (FIGS. 6-7). Similar to tangs 131 and terminal tangs 132, cathode tangs 133 are connected to the flex circuit 130 through traces 136. In the illustrated embodiment, cathode tangs 133 are formed as free floating extensions within the main body 135 of flex circuit 130. A tang 133 that is a free floating extension can have a first end 133a that is attached to the flex circuit 130 and a second end 133b that is unattached. In some embodiments, cathode tangs 133 can be formed as free floating cutouts within a trace 136 such that the trace 136 splits around the tang 133, as illustrated in FIGS. 6-7 with respect to cathode tang 133b. Cathode tangs 133 are capable of movement independent of flex circuit 130, as will be described more fully below.

Referring again to FIG. 5, flex circuit 130 in conjunction with first support portion 120 and capacitors 110a-110c is illustrated. In the illustrated embodiment, first anode tangs 131 are shown being in contact with pins 113 of capacitors 110a-110c. The connection between tangs 131 and pins 113 can be performed by a resistance spot welding ("RSW") or other welding process. Because of the distance between anode pin 113 and the sensitive circuitry within the housing of capacitors 110a-110c, the heat generated by an RSW or other welding process will not damage the sensitive electronics of the capacitors 110a-110c. Terminal tangs 132 are arranged similarly to anode tangs 131, but are present on a different side of the flex circuit 130. Cathode tangs 133 are formed to be proximate the cathode openings 124a-124c of the first support portion 120. In this manner, cathode tangs 133 can be biased, bent or otherwise formed to extend through support portion 120 and contact the housing of capacitors 110a-110c. In the illustrated embodiment, cathode tangs 133 directly contact the weld joints 116 of each of the capacitors 110a-110c. Cathode tangs 133 are electrically connected to the cathode of capacitors 110a-110c by this connection, which can be achieved by a RSW or other welding process. The weld joints 116 provide a contact point for the RSW or other connection process such that the cathode tangs 133 securely bond to the cathode of the capacitors 110a-110c.

Referring again to FIG. 2, a fully assembled capacitor assembly 100 according to some embodiments of the present disclosure is illustrated. The second support portion 140 is arranged on top of the flex circuit 130 and provides physical support for tangs 131 and 132. Second support portion 140 can be adhered to the flex circuit 130 by epoxy or other means. In the illustrated embodiment, the second support portion 140 and first support portion 120 secure the flex circuit 130 between them. The cutout formed by sloped portion 118 of capacitors 110a-110c allows the top portion of second support portion 140 to be substantially coplanar with the top portion 119 of capacitors 110a-110c. The sloped portion 118 allows the fully assembled capacitor assembly 100 to occupy a small envelope, thus ensuring a relatively compact ICD.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An electrochemical cell assembly for use in an implantable cardioverter defibrillator (ICD), comprising:

at least one electrochemical cell comprising a base portion mated with a cover portion at a weld joint to form a housing, a cathode, an anode, and a pin extending from the housing, wherein the housing is electrically connected to the cathode and the pin is electrically connected to the anode; a flex circuit comprising a first tang that is electrically connected to the anode, a second tang that is electrically connected to the cathode, and at least two terminal tangs for connection to control circuitry of the ICD;

a first support portion arranged between the at least one capacitor and a first side of the flex circuit such that the at least one capacitor and the flex circuit are spaced a predetermined distance apart, the first support portion defining an opening through which the second tang extends to electrically connect to the cathode; and a second support portion arranged on a second side of the flex circuit, the second support portion comprising a first support side that supports the at least two terminal tangs.

2. The assembly of claim 1, wherein the second tang is electrically connected to the cathode by resistance spot welding the second tang to the weld joint.

3. The assembly of claim 1, wherein the second tang comprises a free floating extension that includes a first end that is attached to the flex circuit and a second end that is unattached, the free floating extension being capable of movement independent of the flex circuit.

4. The assembly of claim 1, wherein the first tang and the two terminal tangs extend substantially perpendicular to a body portion of the flex circuit.

5. The assembly of claim 4, wherein the second tang comprises a free floating extension that includes a first end that is attached to the flex circuit and a second end that is unattached, the free floating extension being capable of movement independent of the flex circuit.

6. The assembly of claim 5, wherein the second tang is formed within a body of a trace of the flex circuit such that the trace is split around the second tang.

7. The assembly of claim 6, wherein the at least one electrochemical cell comprises a sloped portion that defines a cutout, wherein the flex circuit, first support portion and second support portion are arranged within the cutout.

8. The assembly of claim 7, wherein the second tang is electrically connected to the cathode by resistance spot welding the second tang to the weld joint.

9. The assembly of claim 1, wherein the second tang comprises a free floating extension formed within a body of a trace of the flex circuit such that the trace is split around the second tang, the free floating extension including a first end that is attached to the flex circuit and a second end that is unattached.

10. A method for assembling an electrochemical cell assembly for use in an implantable cardioverter defibrillator (ICD), comprising:
arranging at least one electrochemical cell comprising a base portion mated with a cover portion at a weld joint to form a housing, a cathode, an anode, and a pin extending from the housing, wherein the housing is electrically connected to the cathode and the pin is electrically connected to the anode; a flex circuit comprising a first tang that is electrically connected to the anode, a second tang that is electrically connected to the cathode, and at least two terminal tangs for connection to control circuitry of the ICD;
arranging a first support portion between the at least one capacitor and a first side of the flex circuit such that the at least one capacitor and the flex circuit are spaced a predetermined distance apart; and
arranging a second support portion on a second side of the flex circuit, the second support portion comprising a first support side that supports the at least two terminal tangs.

11. The method of claim 10, wherein the first support portion defines an opening through which the second tang extends to electrically connect to the cathode.

12. The method of claim 10, wherein the second tang is electrically connected to the cathode by resistance spot welding the second tang to the weld joint.

13. The method of claim 10, wherein the second tang comprises a free floating extension that includes a first end that is attached to the flex circuit and a second end that is unattached, the free floating extension being capable of movement independent of the flex circuit.

14. The method of claim 10, wherein the first tang and the two terminal tangs extend substantially perpendicular to a body portion of the flex circuit.

15. The method of claim 14, wherein the second tang comprises a free floating extension that includes a first end that is attached to the flex circuit and a second end that is unattached, the free floating extension being capable of movement independent of the flex circuit.

16. An electrochemical cell assembly for use in an implantable cardioverter defibrillator (ICD), comprising:
means for arranging at least one electrochemical cell comprising a base portion mated with a cover portion at a weld joint to form a housing, a cathode, an anode, and a pin extending from the housing, wherein the housing is electrically connected to the cathode and the pin is electrically connected to the anode; a flex circuit comprising a first tang that is electrically connected to the anode, a second tang that is electrically connected to the cathode, and at least two terminal tangs for connection to control circuitry of the ICD;
means for arranging a first support portion between the at least one capacitor and a first side of the flex circuit such that the at least one capacitor and the flex circuit are spaced a predetermined distance apart; and
means for arranging a second support portion on a second side of the flex circuit, the second support portion comprising a first support side that supports the at least two terminal tangs.

17. The assembly of claim 16, wherein the first support portion defines an opening through which the second tang extends to electrically connect to the cathode.

18. The assembly of claim 16, wherein the second tang is electrically connected to the cathode by resistance spot welding the second tang to the weld joint.

19. The assembly of claim 16, wherein the second tang comprises a free floating extension that includes a first end that is attached to the flex circuit and a second end that is unattached, the free floating extension being capable of movement independent of the flex circuit.

20. The assembly of claim 16, wherein the first tang and the two terminal tangs extend substantially perpendicular to a body portion of the flex circuit.

* * * * *